(12) United States Patent
Duarte

(10) Patent No.: US 7,717,117 B2
(45) Date of Patent: May 18, 2010

(54) SURGICAL DRAPING SYSTEM FOR A PATIENT ON AN OPERATING TABLE AND AN ADJACENT MOVABLE MEDICAL TOOL AND RELATED METHODS

(76) Inventor: Luis E. Duarte, 1512 Darlene St., San Angelo, TX (US) 76904

( * ) Notice: Subject to any disclaimer, the term of this patent is extended or adjusted under 35 U.S.C. 154(b) by 289 days.

(21) Appl. No.: 11/242,265

(22) Filed: Oct. 3, 2005

(65) Prior Publication Data

US 2006/0076024 A1   Apr. 13, 2006

Related U.S. Application Data

(60) Provisional application No. 60/615,350, filed on Oct. 1, 2004.

(51) Int. Cl.
*A61B 19/00* (2006.01)
(52) U.S. Cl. ........................ 128/849; 128/853
(58) Field of Classification Search ................. 128/849, 128/850, 851, 852, 853, 854, 855; 250/496.1, 250/497.1; 378/193, 203, 204, 206, 208, 378/210
See application file for complete search history.

(56) References Cited

U.S. PATENT DOCUMENTS

| | | | | |
|---|---|---|---|---|
| 3,820,536 A | * | 6/1974 | Anspach, Jr. ............ 128/202.13 |
| 3,942,523 A | * | 3/1976 | Rudtke ........................ 128/853 |
| 4,627,363 A | * | 12/1986 | Jones ............................ 108/90 |
| 5,429,142 A | * | 7/1995 | Szabo et al. ................. 128/849 |
| 5,445,165 A | * | 8/1995 | Fenwick ...................... 128/849 |
| 5,490,524 A | * | 2/1996 | Williams et al. ............ 128/849 |
| 5,732,712 A | * | 3/1998 | Adair .......................... 128/845 |
| 6,003,328 A | * | 12/1999 | Faries et al. .................... 62/342 |
| 6,105,578 A | * | 8/2000 | Sommers et al. ............ 128/849 |
| 6,298,855 B1 | | 10/2001 | Baird .......................... 128/849 |
| 6,857,778 B2 | * | 2/2005 | Mun et al. ................... 378/206 |
| 7,044,132 B2 | * | 5/2006 | Masini ........................ 128/849 |
| 7,057,194 B2 | * | 6/2006 | Goldstein ................. 250/515.1 |
| 2003/0028196 A1 | | 2/2003 | Bonutti ....................... 606/87 |
| 2005/0022822 A1 | | 2/2005 | Santilli et al. ............... 128/849 |
| 2006/0235436 A1 | * | 10/2006 | Anderson et al. ........... 606/130 |

* cited by examiner

*Primary Examiner*—Patricia M Bianco
*Assistant Examiner*—Camtu T Nguyen
(74) *Attorney, Agent, or Firm*—Allen, Dyer, Doppelt, Milbrath & Gilchrist, P.A.

(57) ABSTRACT

A surgical draping method for a patient on an operating table and an adjacent movable medical tool may include positioning a patient drape having a surgical access opening in a medial portion thereof over the patient on the operating table so that the surgical access opening exposes a surgical site on the patient. Opposing medial side portions of the patient drape may be fastened together underneath the operating table to provide a pathway thereunder for passage of at least one portion of the medical tool therethrough. An equipment drape may be positioned adjacent a side of the operating table aligned with the pathway to cover the at least one portion of the medical tool when moved through the pathway.

15 Claims, 4 Drawing Sheets

SURGICAL DRAPING SYSTEM FOR A PATIENT ON AN OPERATING TABLE AND AN ADJACENT MOVABLE MEDICAL TOOL AND RELATED METHODS

CROSS-REFERENCE TO RELATED APPLICATIONS

This application claims the benefit of U.S. Provisional Application No. 60/615,350, filed Oct. 1, 2004, which is hereby incorporated herein in its entirety by reference.

FIELD OF THE INVENTION

The present invention relates to the field of surgical devices, and, more particularly, to drapes for use in surgical procedures and related methods.

BACKGROUND OF THE INVENTION

Drapes are used during a variety of surgical procedures to protect sterile surgical zones from microbial invasion. One example of a surgical draping system is disclosed in U.S. Patent Publication No. 2005/0022822 to Santilli et al. This draping system includes a first, closed container within which a first sheet is disposed. The first sheet has first and second opposed ends, the first end of the first sheet being removable from the container to remove a desired portion of the first sheet from the container, the second end of the first sheet remaining within the container. The first container is laid across a desired portion of the table prior to placing the patient on the table. After the patient has been positioned properly and prepped, the first sheet can be pulled from underneath the patient and pulled out of the first container so that the sheet covers the table in the area of surgical interest and then covers the entire side or end of the table down to the floor. A second sheet may also be included to cover other portions of the operating table, as well as a third sheet to cover portions of the patient during pre-operation preparations.

Another surgical draping system is disclosed in published U.S. Patent Publication No. 2003/0028196 to Bonutti. This surgical draping system is intended for use in knee operations and includes a first drape that is positioned over the patient and an operating table so that the patient's leg extends out of an opening in the first drape. A second drape is connected between the first drape and a gown on a surgeon to isolate the patient from the surgeon and/or an assistant. The first and/or second drapes may include attachments for surgical instruments such as suction, Bovie, arthroscopic equipment, etc. The second drape may have a large pouch to collect fluids, blood, etc., so they do not drain onto the floor and are instead collected for disposal. Moreover, the second drape may also include a drain, with or without active suction, to remove fluid and other debris.

Another type of surgery in which drapes play an important role is spinal surgery. During many spinal surgeries, a fluoroscopy (i.e., x-ray) machine is used to take various pictures of the patient's spine. This may be important for determining whether devices implanted in the spine are correctly positioned and installed, for example. A typical fluoroscopy machine used during spinal surgeries has a "C" shape, as illustrated in FIG. 1. This shape allows it to be rotated around the patient's back to take x-rays anteriorly/posteriorly, or from the side of the patient.

A traditional prior art surgical draping system for use in spinal surgery is a large, rectangular drape that covers the patient and hangs down over the sides of operating table. The drape has a surgical access opening therein exposing the patient's back, and the hanging portions of the drape hang approximately to the surgeon's knee level. One significant drawback of this arrangement is that it may be difficult to freely rotate the C-arm underneath and/or around the patient during surgery without brushing the hanging drape. Not only is this an inconvenience, but if the drape were to get caught up with the C-arm, this could lead to movement of the drape, and potentially its removal from the patient. This, in turn, could lead to an increased chance of microbial invasion and, therefore, infection.

SUMMARY OF THE INVENTION

In view of the foregoing background, it is therefore an object of the present invention to provide an improved surgical draping system and related methods.

This and other objects, features, and advantages in accordance with the present invention are provided by a surgical draping method for a patient on an operating table and an adjacent movable medical tool. The method may include positioning a patient drape having a surgical access opening in a medial portion thereof over the patient on the operating table so that the surgical access opening exposes a surgical site on the patient. Moreover, opposing medial side portions of the patient drape may be fastened together underneath the operating table to provide a pathway thereunder for passage of at least one portion of the medical tool therethrough. In addition, an equipment drape may be positioned adjacent a side of the operating table aligned with the pathway to cover the at least one portion of the medical tool when moved through the pathway. Accordingly, the equipment drape advantageously isolates the medical tool from the patient to help maintain a sterile environment around the surgical site, yet while avoiding the need to repeatedly re-drape the medical tool and potentially moving the patient drape out of position.

By way of example, the movable medical tool may be a fluoroscopy machine including a head, a base, and a rotational positioner for rotationally moving the base and head relative to the patient on the operating table. As such, the first equipment drape may be positioned to cover the base of the medical tool when rotated through the pathway, and a second equipment drape may be positioned on the head of the movable medical tool. The method may further include fastening the equipment drape to the patient drape.

The patient drape may also have a proximal end portion and a distal end portion on opposing sides of the medial portion, and the medial portion may have a width less than the widths of the proximal and distal end portions. In addition, the patient drape may also include a reinforcement liner substantially surrounding the surgical access opening. Fastening the medial side portions of the patient drape together may include fastening the medial side portions together with one or more adhesive and/or a hook and loop fasteners.

A surgical draping system for a patient on an operating table and an adjacent movable medical tool in accordance with the invention may include a patient drape having a surgical access opening in a medial portion thereof to be positioned over the patient on the operating table so that the surgical access opening exposes a surgical site on the patient. At least one patient drape fastener may also be included for fastening opposing medial side portions of the patient drape together underneath the operating table to provide a pathway thereunder for passage of at least one portion of the medical tool therethrough. The system may further include an equipment drape to be positioned adjacent a side of the operating table aligned with the pathway to cover the at least one portion of the medical tool when moved through the pathway.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternate embodiments.

Figure 1:
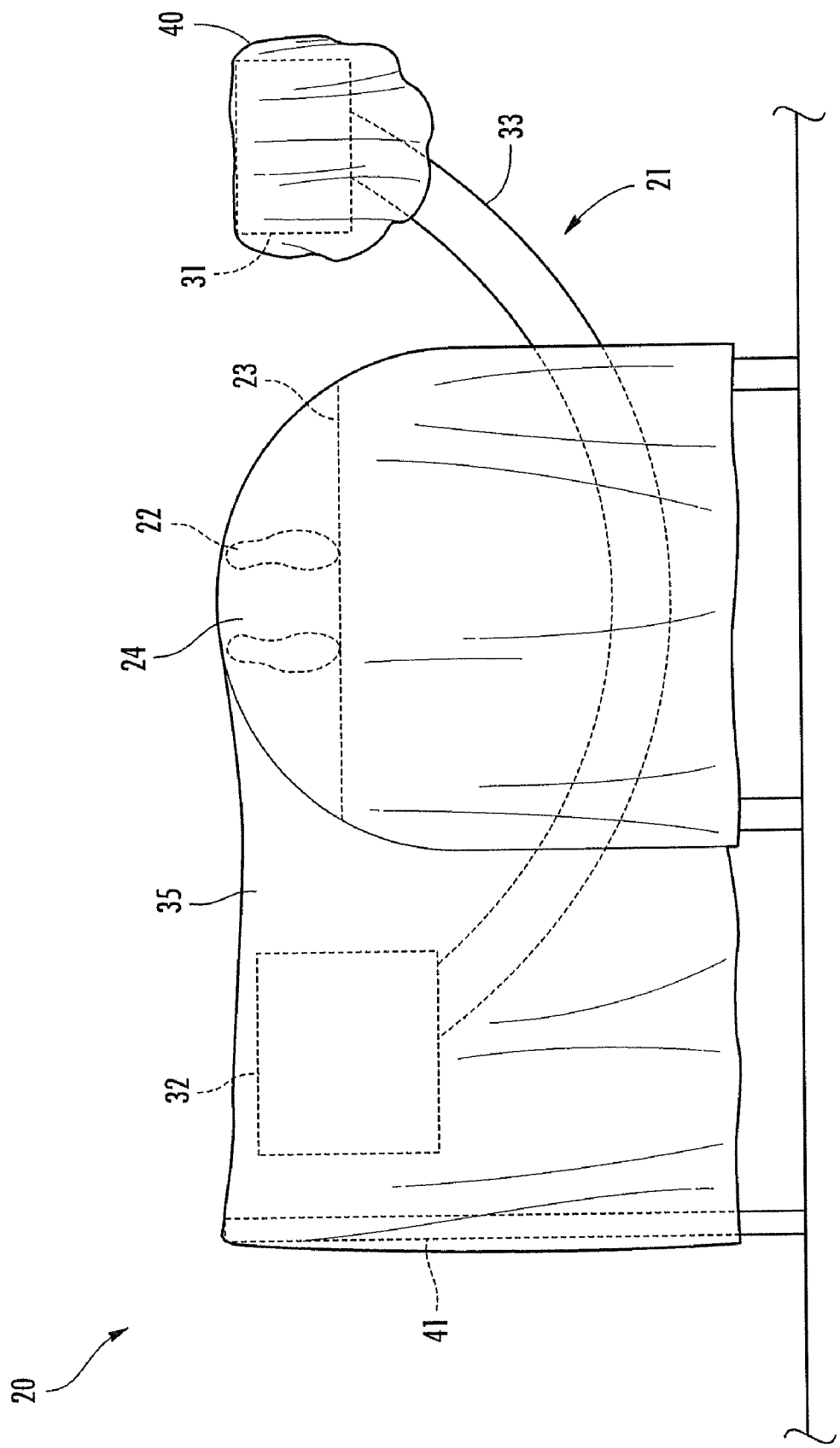
FIG. 1 is an end view of a surgical draping system for a patient on an operating table and an adjacent movable medical tool in accordance with the present invention.
Figure 2:
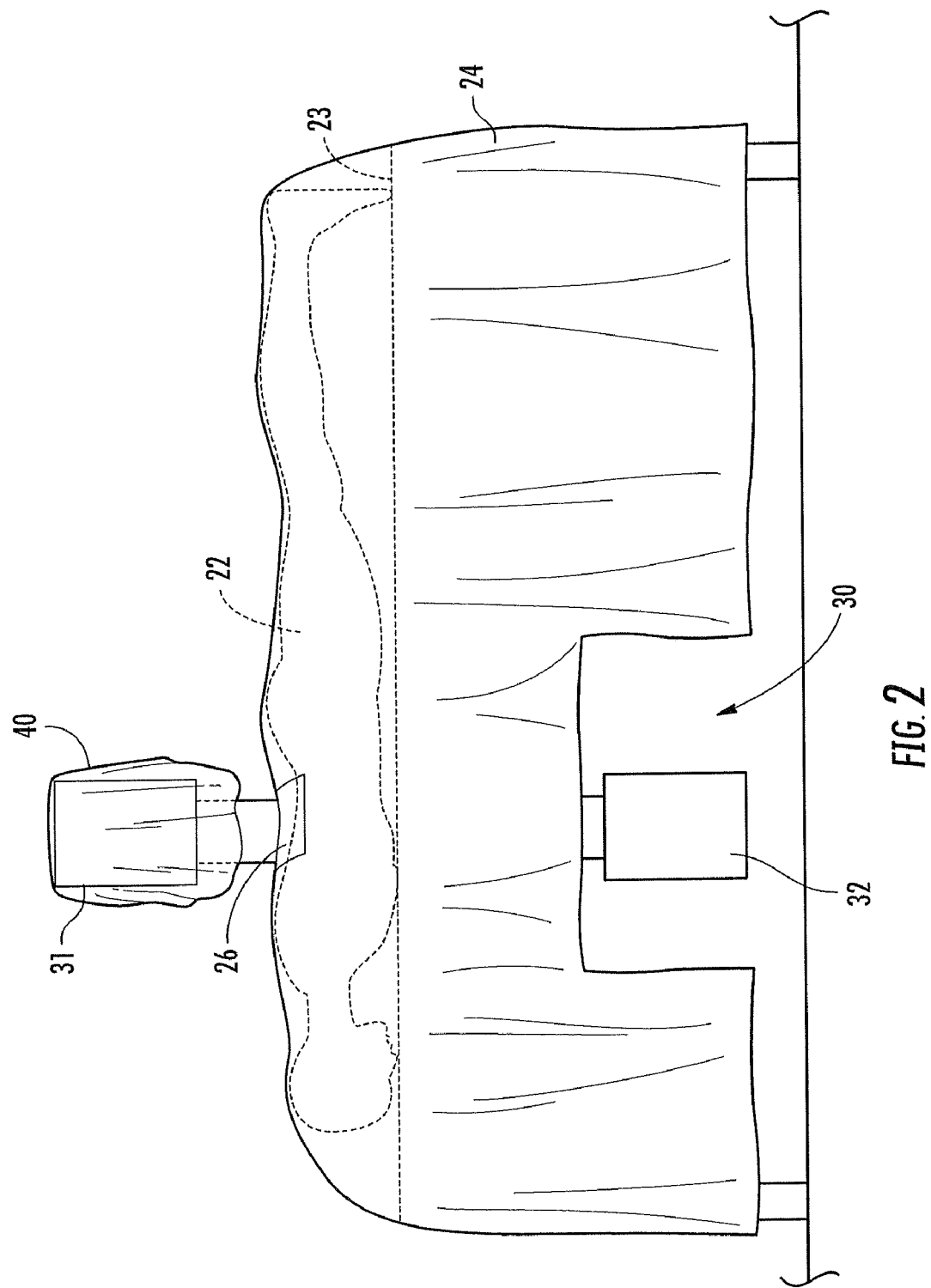
FIG. 2 is a side view of the patient drape of the surgical draping system of FIG. 1.
Figure 3:
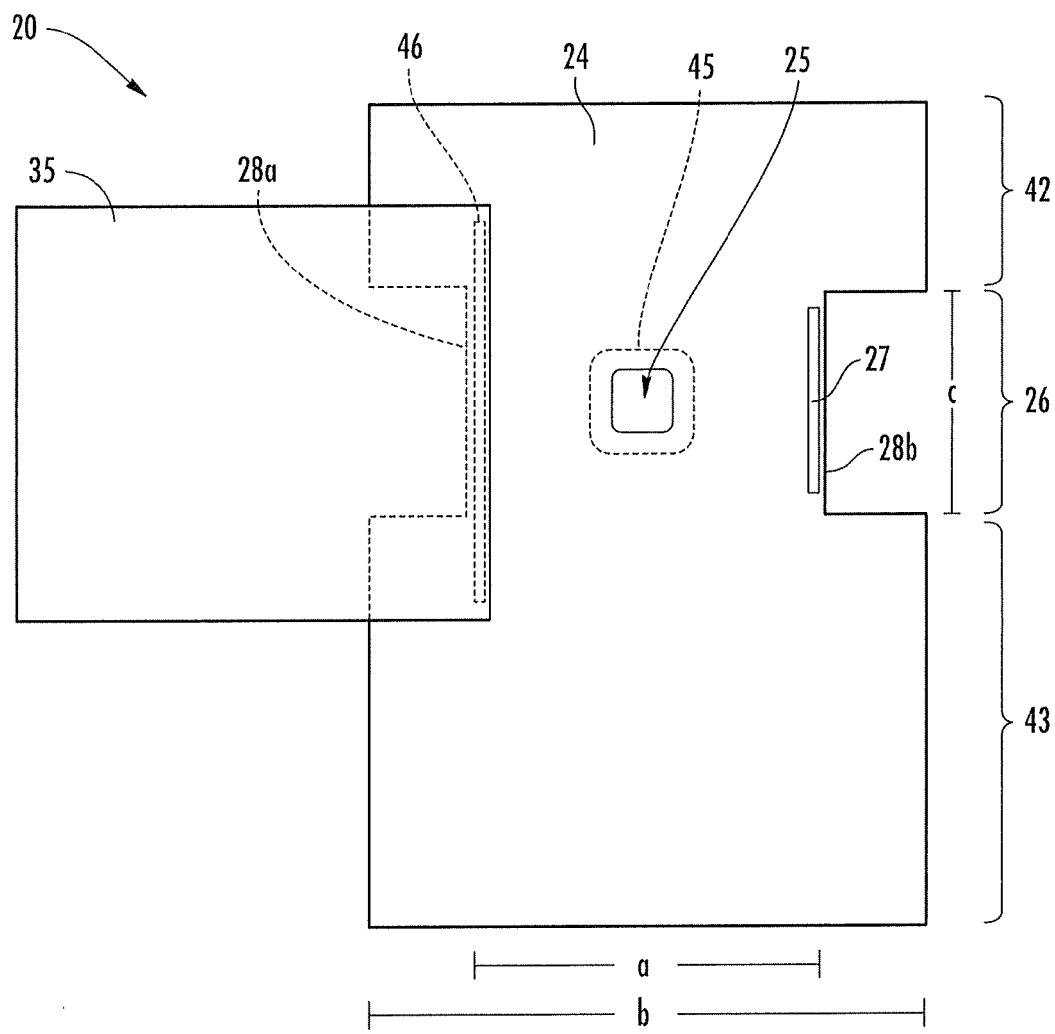
FIG. 3 is a top plan view of the patient drape and first equipment drape of the surgical draping system of FIG. 1.

Referring initially to FIGS. 1-3, the present invention is directed to a surgical draping system 20 for use in operating rooms for procedures requiring a movable surgical tool, such as a fluoroscopy machine 21, for example. The draping system 20 may be used for numerous types of surgical procedures, including spinal surgeries, and it allows free movement of a medical tool such as the illustrated C-arm fluoroscopy machine 21 while maintaining sterility, as will be discussed further below.

The surgical draping system 20 is for a patient 22 on an operating table 23 and an adjacent movable medical tool (i.e., the fluoroscopy machine 21). The fluoroscopy machine 21 illustratively includes a head 31, a base 32, and a rotational positioner (i.e., a C-arm 33) for rotationally moving the base and head relative to the patient 22 on the operating table 23. The fluoroscopy machine 21 also includes a stand that rotationally carries the C-arm 33, although the stand is not shown for clarity of illustration.

The draping system 20 illustratively includes a patient drape 24 having a surgical access opening 25 in a medial portion 26 thereof. The patient drape 24 is to be positioned over the patient 22 on the operating table 23 so that the surgical access opening 25 exposes a surgical site 26 on the patient. One or more patient drape fasteners 27 are used for fastening opposing medial side portions 28a, 28b of the patient drape 24 together underneath the operating table 23. That is, the patient drape 24 wraps around the patient 22 and the operating table 23 and provides a pathway 30 under the operating table 23 for passage of the base 32 and C-arm 33 therethrough. The patient drape 24 may also advantageously help to keep the patient 22 warm. By way of example, the patient drape 24 may be made of any suitable, sterile material such as plastic, cloth, or various synthetic substances. The fastener(s) 27 may be an adhesive, a hook and loop fastener, clips, clamps, or other suitable fasteners.

The draping system 20 further illustratively includes a first equipment drape 35. The equipment drape 25 is to be positioned adjacent a side of the operating table 23 and aligned with the pathway 30 to cover the base 32 and a portion of the C-arm 33 of the fluoroscopy machine 21 when moved through the pathway between a vertical position (FIG. 2) and a lateral position (FIG. 1). The first equipment drape 35 may be made out of similar materials as the patient drape 24. More particularly, a stand 41 holds a side of the first equipment drape 35 farthest away from the patient 22 up to form a "tent" that the base 32 of the fluoroscopy machine 21 moves underneath and into. Various items may be used for the stand 41, such as IV poles, a mayo stand, x-ray holder, etc.

A second equipment drape or cover 40 is positioned on the head 31 of the fluoroscopy machine 21. In the illustrated embodiment the second equipment drape 40 is a made out of a transparent material (e.g., clear plastic), but other suitable sanitary draping/covering materials (cloth, synthetic materials, etc.) may also be used, as will be appreciated by those skilled in the art.

The second equipment drape 40 remains well off the floor while the fluoroscopy machine 21 is moved between the vertical and lateral positions. As such, a single second equipment drape can be used for an entire surgical procedure without re-draping. However, as noted above, putting a similar drape or cover on the base 32 of the fluoroscopy machine 21 is typically not practical as this cover may come in contact with the floor when the fluoroscopy machine is moved between the horizontal and vertical positions, which could render the cover unsanitary.

Moreover, re-draping the base 32 each time it is moved to the lateral position is undesirable as well, as this still places the uncovered base adjacent the exposed surgical site 26 for a short period of time. Moreover, the fluoroscopy machine 21 may be moved between the two positions numerous times during a spinal surgery to take multiple x-rays and make sure implant devices, etc., are properly positioned, for example. As such, continuously re-draping the base 32 with new drapes may be time consuming and expensive.

Yet, by using the first equipment drape 35 as discussed above and shown in FIGS. 1 and 3, the first equipment drape advantageously isolates the fluoroscopy machine 21 from the patient 22 to help maintain a sterile environment around the surgical site 26, yet while avoiding the need to repeatedly re-drape the fluoroscopy machine and potentially moving the patient drape out of position.

The patient drape 24 has a proximal end portion 42 and a distal end portion 43 on opposing sides of the medial portion 26, and the medial portion has a width a less than the width b of the proximal and distal end portions, which in the illustrated embodiment are equal. Of course, it should be noted that the proximal and distal end portions 42, 43 may have unequal widths in different embodiments. By way of example, for a typical surgical application, the width b may be about seventy-six inches, and the width a may be about forty-eight inches. More particularly, the opposing medial side portions 28a, 28b may each be inset about fourteen inches from either side of the patient drape 24, and a length c of the medial portion 26 (and thus the width of the pathway 30) may be about thirty-two inches long. An exemplary overall length of the patient drape 24 may be about one-hundred twenty inches, and exemplary dimensions for the first equipment drape 35 may be about fifty eight by fifty eight inches square. Of course, the above-noted dimensions are merely exemplary, and numerous other sizes, shapes, and dimensions may also be used, as will be appreciated by those skilled in the art.

The patient drape 24 may optionally include a reinforcement liner 45 surrounding or substantially surrounding the surgical access opening. The liner 45 may not only reinforce the area around the surgical access opening 25 to prevent tearing, etc., but it may also have an adhesive thereon to help hold the patient drape 24 in place, as will be appreciated by those skilled in the art. One or more equipment drape fasteners 46 may be used for fastening the equipment drape 35 to the patient drape 24. By way of example, the fastener(s) 46 may be an adhesive, a hook and loop fastener, clips, clamps, or other suitable fasteners.

It should be noted that in some embodiments, the first equipment drape 35 need not be connected to the patient drape 24. For example, the first equipment drape 35 may be a free-standing "tent" with at least a partially open side or bottom so that the base 32 rotates up into the tent in the lateral position to be isolated from the patient 22. In this respect, the first equipment drape 35 need not be made out of the same material as the patient drape, but may instead be made out of a more rigid material (plastic, PVC, etc.), and it may take a variety of shapes.

Figure 4:
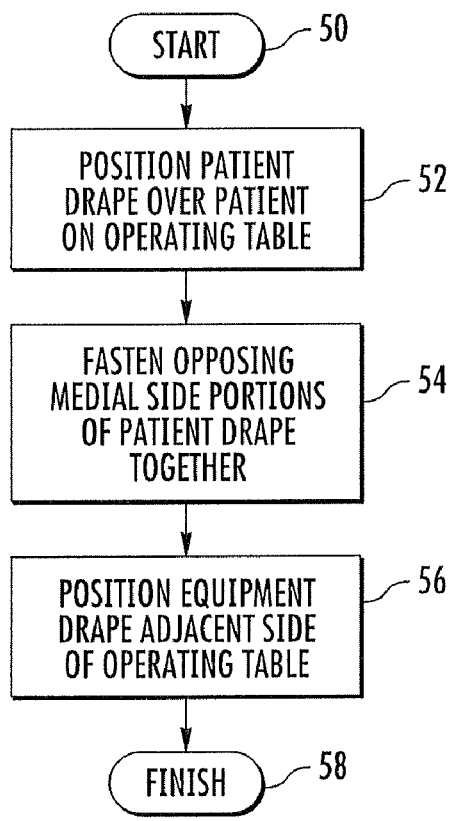
FIGS. 4 and 5 are flow diagrams illustrating surgical draping methods in accordance with the present invention.

Turning to FIG. 4, a surgical draping method for a patient 22 on an operating table 23 and an adjacent movable medical tool (e.g., the fluoroscopy machine 21) is now described. Beginning at Block 50, the method illustratively includes positioning a patient drape 24 having a surgical access opening 25 in a medial portion 26 thereof over the patient 22 on the operating table 23 so that the surgical access opening exposes a surgical site 26 on the patient, at Block 52. Moreover, opposing medial side portions 28a, 28b of the patient drape 24 are fastened together underneath the operating table 23 to provide a pathway 30 thereunder for passage of at least one portion of the medical tool therethrough, at Block 54, as discussed further above. In addition, a first equipment drape 35 is positioned adjacent a side of the operating table 23 aligned with the pathway 30 to cover the at least one portion of the medical tool when moved through the pathway, at Block 56, thus concluding the illustrated method (Block 58).

Figure 5:
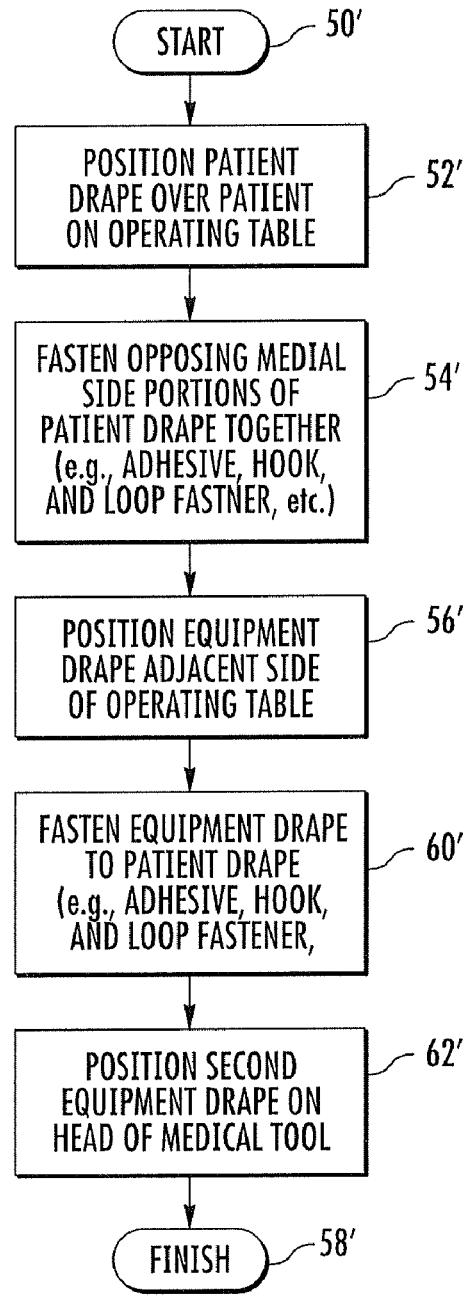

Referring additionally to FIG. 5, additional method aspects may include fastening the first equipment drape 35 to the patient drape 24, at Block 60'. In addition, the method may further include positioning the second equipment drape on the medical tool, e.g., on the head 32 of the fluoroscopy machine 21, at Block 62'.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A surgical draping method for a patient on an operating table and an adjacent movable medical tool comprising:

positioning a patient drape having a surgical access opening in a medial portion thereof over the patient on the operating table so that the surgical access opening exposes a surgical site on the patient, the patient drape also having a proximal end portion and a distal end portion on opposing sides of the medial portion, and the patient drape having insets on opposing sides of the medial portion so that the medial portion has a width less than the widths of the proximal and distal end portions;

fastening opposing medial side portions of the patient drape together underneath the operating table to provide a pathway thereunder for passage of at least one portion of the moveable medical tool therethrough;

positioning an equipment drape adjacent a side of the operating table aligned with the pathway to cover the at least one portion of the moveable medical tool when moved through the pathway; and positioning a second equipment drape on the movable medical tool.

2. The method of claim 1 wherein fastening the medial side portions of the patient drape together comprises fastening the medial side portions together with an adhesive.

3. The method of claim 1 wherein fastening the medial side portions of the patient drape together comprises fastening the medial side portions together with a hook and loop fastener.

4. The method of claim 1 further comprising fastening the equipment drape to the patient drape.

5. The method of claim 1 wherein the movable medical tool comprises a fluoroscopy machine.

6. The method of claim 1 wherein the patient drape comprises a reinforcement liner substantially surrounding the surgical access opening.

7. A surgical draping method for a patient on an operating table and an adjacent moveable medical tool including a base, an opposing head and a rotational positioner for rotationally moving the base and head relative to the patient on the operating table, the method comprising:

positioning a patient drape having a surgical access opening in a medial portion thereof over the patient on the operating table so that the surgical access opening exposes a surgical site on the patient, the patient drape also having a proximal end portion and a distal end portion on opposing sides of the medial portion, and the patient drape having insets on opposing sides of the medial portion so that the medial portion has a width less than the widths of the proximal and distal end portions;

fastening opposing medial side portions of the patient drape together underneath the operating table to provide a pathway thereunder for passage of the base of the medical tool therethrough;

positioning a first equipment drape adjacent a side of the operating table aligned with the pathway to cover the base of the moveable medical tool when rotated through the pathway; and positioning a second equipment drape on the head of the movable medical tool.

8. The method of claim 7 further comprising fastening the first equipment drape to the patient drape.

9. The method of claim 7 wherein the movable medical tool comprises a fluoroscopy machine.

10. The method of claim 7 wherein the patient drape comprises a reinforcement liner substantially surrounding the surgical access opening.

11. A surgical draping system for a patient on an operating table and an adjacent movable medical tool comprising:

a patient drape having a surgical access opening in a medial portion thereof positioned over the patient on the operating table so that the surgical access opening exposes a surgical site on the patient, said patient drape also having a proximal end portion and a distal end portion on opposing sides of the medial portion, and the patient drape having insets on opposing sides of the medial portion so that the medial portion has a width less than the widths of the proximal and distal end portions;

at least one patient drape fastener fastening opposing sides of the medial portion of the patient drape together underneath the operating table to provide a pathway thereunder for passage of at least one portion of the moveable medical tool therethrough;

an equipment drape positioned adjacent a side of the operating table aligned with the pathway to cover the at least one portion of the movable medical tool when moved through the pathway; and a second equipment drape on the movable medical tool.

12. The surgical draping system of claim 11 further comprising at least one equipment drape fastener fastening the equipment drape to the patient drape.

13. The surgical draping system of claim 11 wherein the movable medical tool comprises a fluoroscopy machine.

14. The surgical draping system of claim 11 wherein the patient drape comprises a reinforcement liner substantially surrounding the surgical access opening.

15. The surgical draping system of claim 11 wherein said at least one patient drape fastener comprises at least one of an adhesive and a hook and loop fastener.

* * * * *